United States Patent
Fujii et al.

(10) Patent No.: US 8,494,228 B2
(45) Date of Patent: Jul. 23, 2013

(54) PERSONAL AUTHENTICATION METHOD USING SUBCUTANEOUS BLOODSTREAM MEASUREMENT AND PERSONAL AUTHENTICATION DEVICE

(75) Inventors: Hitoshi Fujii, Kitakyushu (JP); Kenji Okamoto, Iizuka (JP)

(73) Assignees: Kyushu Institute of Technology, Fukuoka (JP); Syscom Japan, Inc., Fukuoka (JP)

( * ) Notice: Subject to any disclaimer, the term of this patent is extended or adjusted under 35 U.S.C. 154(b) by 462 days.

(21) Appl. No.: 12/936,142

(22) PCT Filed: Mar. 23, 2009

(86) PCT No.: PCT/JP2009/055580
§ 371 (c)(1),
(2), (4) Date: Oct. 1, 2010

(87) PCT Pub. No.: WO2009/122931
PCT Pub. Date: Oct. 8, 2009

(65) Prior Publication Data
US 2011/0026783 A1 Feb. 3, 2011

(30) Foreign Application Priority Data
Apr. 3, 2008 (JP) .................................. 2008-096679

(51) Int. Cl.
*G06K 9/62* (2006.01)
(52) U.S. Cl.
USPC ........................................................ 382/115
(58) Field of Classification Search
None
See application file for complete search history.

(56) References Cited

U.S. PATENT DOCUMENTS

| 4,862,894 A | * | 9/1989 | Fujii | ............................. | 600/479 |
| 5,588,437 A | | 12/1996 | Byrne et al. | | |
| 7,364,821 B2 | * | 4/2008 | You | .................................. | 430/5 |
| 2007/0177772 A1 | | 8/2007 | Fujii et al. | | |
| 2008/0260211 A1 | * | 10/2008 | Bennett et al. | ................ | 382/115 |
| 2010/0168585 A1 | * | 7/2010 | Fujii et al. | ..................... | 600/476 |

FOREIGN PATENT DOCUMENTS

| JP | 5-28133 B2 | 9/1988 |
| JP | 5-028134 B2 | 5/1989 |
| JP | 4-504213 A | 7/1992 |
| JP | 04-242628 A | 8/1992 |
| JP | 05-073666 A | 3/1993 |
| JP | 08-016752 A | 1/1996 |
| JP | 08-112262 A | 5/1996 |

(Continued)

Primary Examiner — Brian P Werner
(74) Attorney, Agent, or Firm — Sughrue Mion, PLLC (57) ABSTRACT

In a personal authentication method using the subcutaneous bloodstream measurement where an expanded laser beam is irradiated onto a finger pad, light reflected from a subcutaneous blood vessel layer is imaged on an image sensor as a laser speckle using an optical system, a quantity that represents the rate of change with respect to time of the amount of light received for each pixel of the laser speckle is calculated, the values are used as a two-dimensional map to obtain a map showing the bloodstream of the finger pad, and the bloodstream map is comparison-checked against pre-registered data of individuals, the laser speckle is imaged on the image sensor using a region separate from a region irradiated by the laser beam as an observation region of the image sensor. A device for use in the method is also provided. Relating to a method and device for authentication using, e.g., a finger print pattern on the basis of the laser speckle, an improved technique capable of extracting, e.g., the finger print pattern accurately is provided.

10 Claims, 3 Drawing Sheets

FOREIGN PATENT DOCUMENTS

| | | |
|---|---|---|
| JP | 2003-164431 A | 6/2003 |
| JP | 2003-180641 A | 7/2003 |
| JP | 2003-331268 A | 11/2003 |
| JP | 2006-026427 A | 2/2006 |
| JP | 2008-054787 A | 3/2008 |
| WO | 2005/122896 A1 | 12/2005 |
| WO | 2007/027579 A2 | 3/2007 |
| WO | 2007/097129 A1 | 8/2007 |

* cited by examiner

PERSONAL AUTHENTICATION METHOD USING SUBCUTANEOUS BLOODSTREAM MEASUREMENT AND PERSONAL AUTHENTICATION DEVICE

TECHNICAL FIELD

The present invention relates to a personal authentication method characterized by measuring the subcutaneous bloodstream and a device for using the method. Particularly, the present invention relates to a method and device for extracting a pattern corresponding to a fingerprint from a bloodstream map of a finger pad to authenticate a person.

BACKGROUND ART

For personal authentication based on a fingerprint, various methods of inputting a pattern as an image into a computer by using a laser or the like and analyzing the pattern image have been developed up to the present date in place of an old-established method based on visual check. A large number of techniques for a sensor section for detecting a fingerprint have been proposed; for example, there have been practically used an optical method of directly taking a fingerprint pattern into an image sensor by combining the difference in scattering angle between a ridge and a recess with a total reflection condition and a method of extracting a pattern by utilizing a semiconductor sensor for detecting the difference in charge distribution on a contact surface. Furthermore, a method of extracting a vein pattern of a fingertip or a palm by using near-infrared light to perform personal authentication has been proposed and the product using the method has been manufactured (e.g., Patent document 1-3). Since a fingerprint pattern is more complicated in shape compared with a vein pattern, the methods have a possibility of constituting a personal authentication system with higher accuracy. However, there is a risk that authentication may be violated by counterfeiting the same shape as a finger pad, for example, by transcribing a fingerprint to a mold made of a material such as silicone.

When a laser beam is irradiated to a living body, an intensity distribution of reflected and scattering light forms dynamic laser speckles (random speckled pattern) due to moving scattering particles such as blood cells. It is known that this pattern is detected on an imaging plane by an image sensor, and time variation of the pattern at each pixel is quantified and displayed in the form of a map, whereby a bloodstream distribution of capillary blood vessels in the vicinity of the surface of the living body can be imaged. Using such a phenomenon, a certain number of techniques and devices for measuring a bloodstream map of a subcutaneous layer or an ocular fundus have been proposed by the present inventors (e.g., Patent document 1-3).

The present inventors accomplished inventions of combining the bloodstream map disclosed in the above-mentioned documents and a fingerprint pattern for performing personal authentication, and have already proposed them (Patent document 10 and 11). In these patent documents, authentication of a finger of a living person is performed using phenomenon that, when the bloodstream of a fingertip is imaged using a laser bloodstream imaging method, a fingerprint pattern appears in a bloodstream map since a bloodstream in a recess portion of the fingerprint is faster than that in a ridge portion (Patent Document 10). Also, there has been proposed a method of detecting the internal bloodstream distribution of a finger by using a near-infrared laser light so as to improve accuracy on personal authentication and exclusion of other persons or a method of determining a living finger or an imitated finger by analyzing a waveform of the bloodstream since the bloodstream of a fingertip varies in synchronism with heart beat (Patent document 11).

However, these methods are still problematic in that, when a very thin silicone film having a counterfeited fingerprint with ridge-and-recess pattern is affixed to a surface of finger, a sensor perceives the bloodstream of the finger behind the film and determines it wrongly as being alive. Also, there is a problem that, in winter season with a low room temperature, a living finger is wrongly determined as a counterfeited finger since the fingertip becomes cold, the bloodstream of the surface thereof decreases and the waveform of the bloodstream becomes difficult to be detected. To the best of the present inventors' knowledge, there has not yet been proposed any method and device to overcome these problems described above.

Patent document 1: JP-A-5-73666 (JP-A denotes a Japanese unexamined patent publication)
Patent document 2: JP-A-8-16752
Patent document 3: JP-A-2003-331268
Patent document 4: JP-B-5-28133 (JP-B denotes a Japanese examined patent publication)
Patent document 5: JP-B-5-28134
Patent document 6: JP-A-4-242628
Patent document 7: JP-A-8-112262
Patent document 8: JP-A-2003-164431
Patent document 9: JP-A-2003-180641
Patent document 10: WO05/122896
Patent document 11: WO07/097,129

DISCLOSURE OF INVENTION

Problems to be Solved by the Invention

Personal authentication method and device utilizing, e.g., a fingerprint on the basis of laser speckles of a finger pad have a risk that, upon using a counterfeited finger having a film made of silicone etc. with ridge-and-recess pattern imitating a fingerprint affixed to a fingertip, the counterfeited finger may be wrongly authenticated as a fingerprint of a living body. Also, there is a problem that, in winter season with a low room temperature, a living finger may be wrongly determined as a counterfeited finger since the fingertip becomes cold and the bloodstream of the surface thereof decreases, thereby it becomes difficult to detect heart beat components. The present invention aims to provide a personal authentication method and device with higher accuracy in which the problems mentioned above are solved.

Means for Solving the Problems

In order to determine a living finger, it is necessary to detect accurately a bloodstream variation in synchronism with heart beat. The present inventors have found that, to that end, it is better to measure the bloodstream in an internal portion rather than in a surface layer portion of the skin and have created the following technical matters to realize the above knowledge.

(1) When a laser irradiating portion is apart from an observation region of an image sensor, more light signal components can be detected through an internal portion of the skin.

(2) When a laser is propagated a long enough distance through an internal portion of a finger by either a method of irradiating the laser to the finger pad and arranging an observation region of an image sensor in the fingertip side or a method of irradiating the laser to the fingertip side and arranging an observation region of an image sensor in the finger pad, an internal bloodstream variation can be detected accurately.

(3) When a film having a high degree of scattering and no bloodstream is affixed to the surface of a finger, a fixed pattern is superimposed on a pattern imaged on an image sensor plane due to interference of laser waves scattered and an average difference of intensities detected at neighboring pixels increases, then making it possible to discern an imitated finger by using the difference of intensities detected at neighboring pixels.

The problems mentioned above can be solved by the present inventions described in embodiments 1-14 on the basis of the technical knowledge mentioned above of the present inventors.

Among the present inventions, the invention described in embodiment 1 is a personal authentication method through the measurement of the subcutaneous bloodstream comprising:
- expanding a laser beam and irradiating the expanded laser beam to a finger pad;
- focusing light reflected from a subcutaneous blood vessel layer onto an image sensor plane as laser speckles by using an optical system;
- determining an amount representing a rate of time variation of the amount of received light at each pixel point in the laser speckles and setting a numerical value thus obtained as a two-dimensional map to thereby obtain a bloodstream map of the finger pad; and
- comparison-checking a fingerprint pattern appearing as the bloodstream map with pre-registered personal data for authentication,
- wherein said laser speckles are focused onto the image sensor plane using a region separate from a region irradiated by the laser beam as an observation region of the image sensor.

The invention described in embodiment 2 is the personal authentication method through the measurement of the subcutaneous bloodstream according to embodiment 1, wherein the laser beam forms a linear spot, the image sensor is a linear sensor and the linear spot is arranged in parallel with an observation region of the linear sensor.

The invention described in embodiment 3 is the personal authentication method through the measurement of the subcutaneous bloodstream according to embodiment 1, wherein the laser beam is irradiated to a center portion of the finger pad and the observation region of the image sensor is arranged in a fingertip side of the finger pad.

The invention described in embodiment 4 is the personal authentication method through the measurement of the subcutaneous bloodstream according to embodiment 1, wherein the laser beam is irradiated to a fingertip portion of the finger pad and the observation region of the image sensor is arranged in a center portion of the finger pad.

The invention described in embodiment 5 is the personal authentication method through the measurement of the subcutaneous bloodstream according to any one of embodiments 1-4, wherein the method further includes a function of detecting a counterfeited finger by detecting a signal waveform representing an intensity distribution of an amount of light received at each pixel of at least one row in the image sensor plane and comparing the signal waveform with a pre-set signal waveform of a living finger.

The invention described in embodiment 6 is a personal authentication device through the measurement of the subcutaneous bloodstream comprising:
- one or two irradiating means for expanding a laser beam and irradiating the expanded laser beam to a finger pad;
- light receiving means that has many pixels and receives light reflected from a subcutaneous blood vessel layer of the finger pad;
- storage means for storing the output of each pixel achieved by the light receiving means;
- calculation means for calculating an amount representing a rate of time variation of light intensity received at each pixel from storage content of the storage means;
- second storage means for storing a two-dimensional distribution of a calculation result achieved at each pixel as a bloodstream map; and
- means for comparing the bloodstream map stored in the second storage means with pre-registered personal data for authentication,
- wherein a region for irradiating the expanded laser beam in said irradiating means is arranged separate from an observation region of an image sensor for reflected light in said light receiving means.

The invention described in embodiment 7 is the personal authentication device through the measurement of the subcutaneous bloodstream according to embodiment 6, wherein the device further includes a means for detecting a counterfeited finger by detecting a signal waveform representing an intensity distribution of an amount of light received at each pixel of at least one row in the image sensor plane and comparing the signal waveform with a pre-set signal waveform of a living finger.

The invention described in embodiment 8 is a personal authentication method through the measurement of the subcutaneous bloodstream comprising:
- expanding a laser beam and irradiating the expanded laser beam to a finger pad;
- focusing light reflected from a subcutaneous blood vessel layer onto an image sensor plane as laser speckles by using an optical system;
- determining an amount representing a rate of time variation of light intensity received at each pixel point in the laser speckles and setting a numerical value thus obtained as a two-dimensional map to thereby obtain a bloodstream map of the finger pad;
- comparison-checking a fingerprint pattern appearing as a bloodstream map with pre-registered personal data for authentication; and
- calculating time variation of an average bloodstream in the whole area or some area, and comparing the time variation concerned with a predetermined reference for authentication,
- wherein said laser speckles are focused onto the image sensor plane using a region separate from a region irradiated by the laser beam as an observation region of the image sensor.

The invention described in embodiment 9 is a personal authentication device through the measurement of the subcutaneous bloodstream comprising:
- one or two irradiating means for expanding a laser beam and irradiating the expanded laser beam to a finger pad;
- light receiving means that has many pixels and receives light reflected from a subcutaneous blood vessel layer of the finger pad;
- storage means for storing the output of each pixel achieved by the light receiving means;
- calculation means for calculating an amount representing a rate of time variation of light intensity received at each pixel from storage content of the storage means;
- second storage means for storing a two-dimensional distribution of a calculation result achieved at each pixel as a bloodstream map;

means for comparing the bloodstream map stored in the second storage means with pre-registered personal data for authentication;

means for calculating time variation of an average bloodstream in the whole area or some area and comparing the time variation concerned with a predetermined reference for authentication, wherein a region for irradiating the expanded laser beam in said irradiating means is arranged separate from an observation region of the image sensor for reflected light in said light receiving means.

The invention described in embodiment 10 is the personal authentication device through the measurement of the subcutaneous bloodstream according to embodiment 9, wherein the device further includes means for detecting a counterfeited finger by detecting a signal waveform representing an intensity distribution of an amount of light received at each pixel of at least one row in the image sensor plane and comparing the signal waveform with a pre-set signal waveform of a living finger.

The invention described in embodiment 11 is a personal authentication method through the measurement of the subcutaneous bloodstream comprising:

expanding a laser beam and irradiating the expanded laser beam to a finger pad;

focusing light reflected from a subcutaneous blood vessel layer onto an image sensor plane as laser speckles by using an optical system;

determining an amount representing a rate of time variation of light intensity received at each pixel point in the laser speckles and setting the numerical value thus achieved as a two-dimensional map to thereby achieve a bloodstream map of the finger pad; and comparison-checking a fingerprint pattern appearing as a bloodstream map with pre-registered personal data for authentication, wherein the method further includes a function for detecting a counterfeited finger by detecting a signal waveform representing an intensity distribution of an amount of light received at each pixel of at least one row in the image sensor plane at appropriate time, that is, before, after or during those operations mentioned above and comparing the signal waveform with a pre-set signal waveform of a living finger.

The invention described in embodiment 12 is a personal authentication device through the measurement of the subcutaneous bloodstream comprising:

one or two irradiating means for expanding a laser beam and irradiating the expanded laser beam to a finger pad;

light receiving means that has many pixels and receives light reflected from a subcutaneous blood vessel layer of the finger pad;

storage means for storing the output of each pixel achieved by the light receiving means;

calculation means for calculating an amount representing a rate of time variation of light intensity received at each pixel from storage content of the storage means;

second storage means for storing a two-dimensional distribution of the calculation result achieved at each pixel as a bloodstream map; and means for comparing the bloodstream map stored in the second storage means with pre-registered personal data for authentication, wherein the device further includes a means for detecting a counterfeited finger by detecting a signal waveform representing an intensity distribution of an amount of light received at each pixel of at least one row in the image sensor plane and comparing the signal waveform with a pre-set signal waveform of a living finger.

The invention described in embodiment 13 is a personal authentication method through the measurement of the subcutaneous bloodstream comprising:

expanding a laser beam and irradiating the expanded laser beam to a finger pad;

focusing light reflected from a subcutaneous blood vessel layer onto an image sensor plane as laser speckles by using an optical system;

determining an amount representing a rate of time variation of light intensity received at each pixel point in the laser speckles and setting the numerical value thus achieved as a two-dimensional map to thereby achieve a bloodstream map of the finger pad; and comparison-checking a fingerprint pattern appearing as the bloodstream map with pre-registered personal data for authentication, wherein the laser beam is irradiated to the finger pad through a masking shield with a number of horizontally-long slits to form a lattice-shaped laser spot, the spot is arranged in substantially the same direction as a scanning line of the sensor, and data on the spot is analyzed to detect the bloodstream map of a surface layer of the finger pad and the time variation thereof or data between each spot is analyzed to detect the bloodstream map of an internal layer of the finger pad and the time variation thereof.

The invention described in embodiment 14 is a personal authentication method through the measurement of the subcutaneous bloodstream comprising:

expanding a laser beam and irradiating the expanded laser beam to a finger pad;

focusing light reflected from a subcutaneous blood vessel layer onto an image sensor plane as laser speckles by using an optical system;

determining an amount representing a rate of time variation of light intensity received at each pixel point in the laser speckles and setting a numerical value thus obtained as a two-dimensional map to thereby obtain a bloodstream map of the finger pad;

comparison-checking a fingerprint pattern appearing as the bloodstream map with pre-registered personal data for authentication; and calculating time variation of an average bloodstream in the whole area or some area, and comparing the time variation concerned with a predetermined reference for authentication, wherein the laser beam is irradiated to the finger pad through a masking shield with a number of horizontally-long slits to form a lattice-shaped laser spot, the spot is arranged in substantially the same direction as a scanning line of the sensor, and data on the spot is analyzed to detect the bloodstream map of the surface layer of the finger pad and the time variation thereof or data between each spot is analyzed to detect the bloodstream map and the time variation thereof.

Effects of the Invention

A personal authentication technique utilizing, e.g., a fingerprint pattern on the basis of laser speckles of a finger pad is characterized by drawing the fingerprint pattern using bloodstream information inherent to a living body and utilizes the fact that the pattern concerned varies with time in synchronism with heart beat, and it is very difficult to counterfeit such a model based on the combination of the two-dimensional pattern and the time axis as described above. However, such a technique has still been problematic in that a counterfeited finger made of silicone resin etc. with a ridge-and-recess pattern imitating a fingerprint or a film made of silicone etc. with a ridge-and-recess pattern imitating a fingerprint affixed to a finger may be wrongly authenticated as a true finger. According to the present invention, it makes it possible to distinguish an imitated finger clearly from a normal finger of an individual since bloodstream information of the interior of the finger can be taken out accurately and also an internal bloodstream signal can surely be detected even when the bloodstream decreases due to coldness in a cold area or the like.

BRIEF DESCRIPTION OF DRAWINGS (FIG. 1) A conceptual diagram showing a personal authentication technique based on laser speckles in the conventional art.

BEST MODE TO CARRY OUT THE INVENTION

Information achieved from the bloodstream, out of information concerning a living body, has a feature that makes it impossible to identify a person unless a sensor works on the person while the person is alive. A personal authentication method utilizing, e.g., a fingerprint based on laser speckles of a finger pad is a technique of measuring the subcutaneous bloodstream which is modulated spatially by the ridge-and-recess pattern of a fingerprint by a bloodstream measurement technique using laser scattering. In order to measure the subcutaneous bloodstream, a laser beam is first expanded and irradiated to a finger pad, and light reflected from a blood vessel layer under the skin is focused as laser speckles onto an image sensor plane using an optical system. The laser speckles are continuously scanned by using the image sensor, an amount representing a rate of time variation of light intensity received at each pixel, for example, an average time variation rate, or a reciprocal of the variation of the received light amount which is integrated in accordance with the exposure time of the image sensor is determined, and then the numerical value thus achieved is set as a two-dimensional map to thereby achieve a bloodstream map of the finger pad. Subsequently, a fingerprint pattern appearing as a bloodstream map is compared with pre-registered personal data and identified. In another mode, a step for determining the time variation of the average bloodstream in the whole area or some area, and comparing the time variation thus determined with a predetermined reference for identification is added to the above-described process. Further, there may be incorporated a step for displaying the bloodstream map or the fingerprint pattern thus achieved, or displaying means may be incorporated to the above-described process as necessary.

The present invention improves the above-described personal authentication technique utilizing, e.g., a fingerprint pattern based on laser speckles of a finger pad and is a personal authentication method characterized in that laser speckles are focused on an image sensor plane using a region apart from a laser beam irradiating region as an observation region of the image sensor for reflective light. Also, the present invention is a personal authentication device used for the method of personal authentication.

Figure 1:
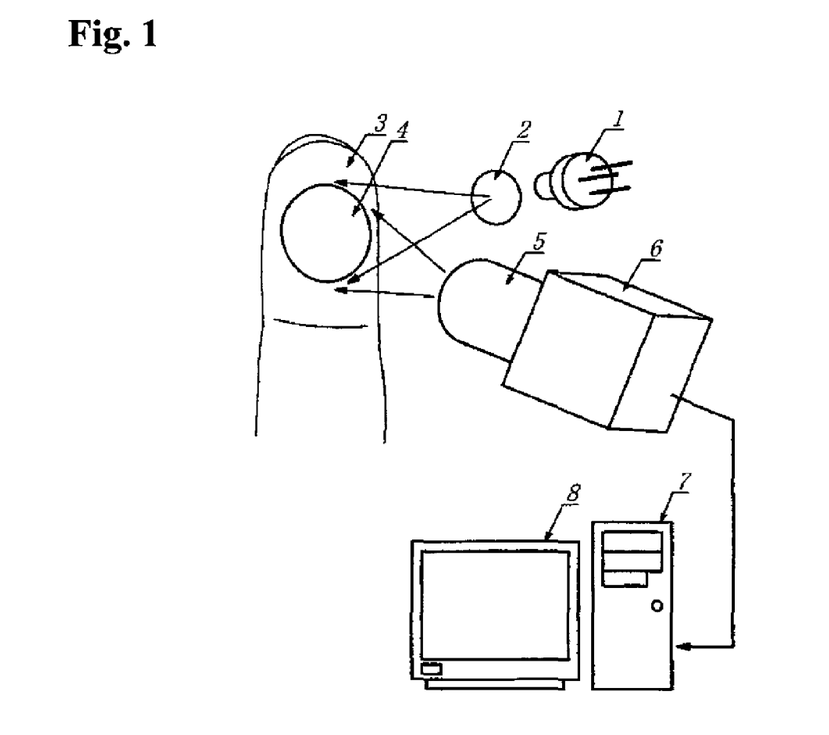

FIG. 1 is a conceptual diagram showing a personal authentication technique using a fingerprint pattern or the like based on laser speckles by the measurement of the bloodstream of a finger in prior arts. Numeral 1 denotes a small-sized laser light source such as semiconductor laser, 2 denotes an optical system, 3 denotes a finger pad, 4 denotes a laser spot (an irradiating spot) or an observation region, 5 denotes an imaging optical system, 6 denotes an image sensor or CCD camera, 7 denotes a personal computer for analysis and 8 denotes a display.

As shown in FIG. 1, for example, light emitted from a small laser light source such as a semiconductor laser is expanded through an optical system, and is irradiated to a wide area of the finger pad 3 (the irradiating spot 4). This irradiating spot is focused on a light-receiving plane of the image sensor or CCD camera 6, etc. through the imaging optical system 5. Image signals obtained from the image sensor or CCD camera are subjected to A/D conversion and taken into a personal computer 7, and an amount representing a rate of time variation of light intensity received at each pixel point, for example, an average time variation rate, or a reciprocal of the magnitude of the variation in the amount of light received integrated over the exposure time of the image sensor is calculated, and displayed in the form of a map to achieve the necessary bloodstream map data.

In the thus-obtained map of the bloodstream of the subcutaneous capillary blood vessels of the finger pad, a fingerprint pattern appears. This data is compared with pre-registered data to perform personal authentication. A method/means of comparing and checking the fingerprint pattern appeared as the bloodstream map with the pre-registered personal data is not limited to a special one, and a conventionally known method/means may be used.

By the way, in the conventional method and device shown in FIG. 1, since the laser spot overlaps the observation viewing field, image sensor 6 detects reflected light which scatters toward the camera from a surface layer portion of the finger in a higher ratio than reflected light which diffuses into a subcutaneous deep tissue portion of the finger and then returns to the surface. Therefore, there is a problem that a bloodstream variation of the subcutaneous tissue cannot be detected efficiently.

Figure 2:
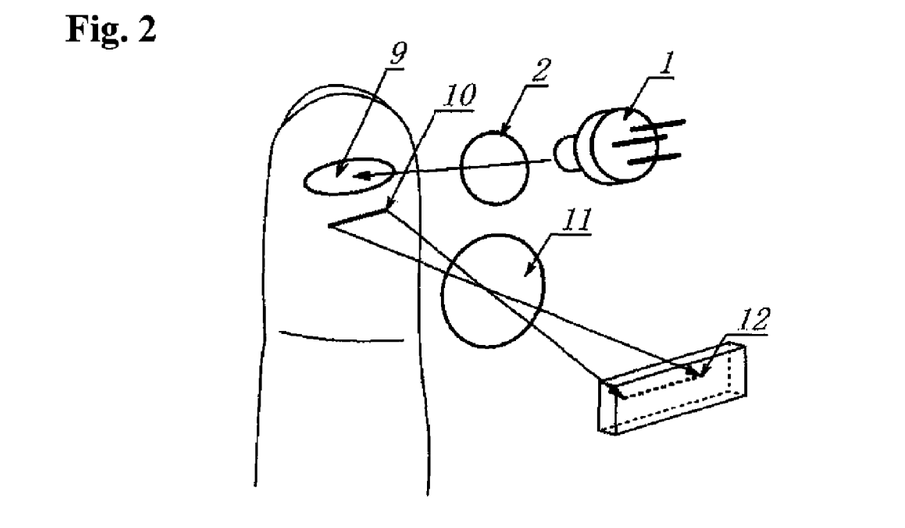
(FIG. 2) A conceptual diagram showing a personal authentication technique based on laser speckles according to the present invention.
Figure 3:
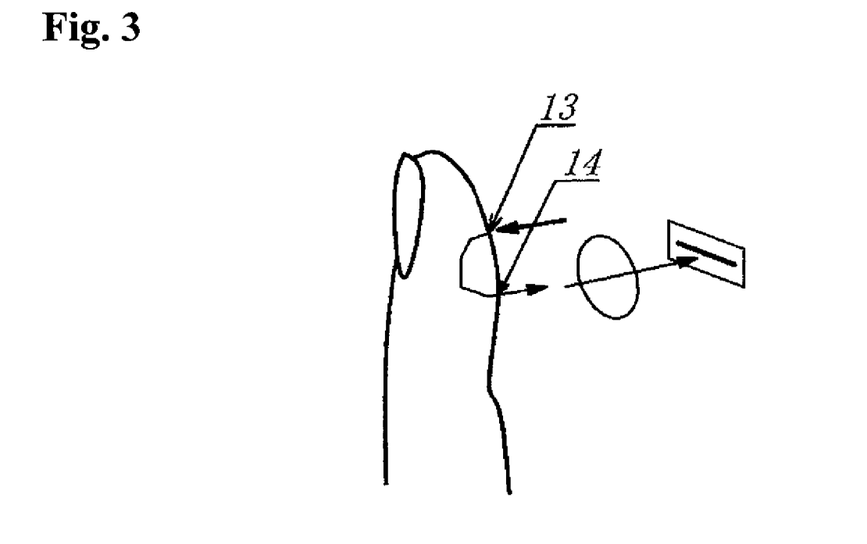
(FIG. 3) A diagram showing one example of a relationship of a laser irradiating spot and an observation position of an image sensor according to the present invention.

FIG. 2 is a conceptual diagram showing a technique in which laser speckles are focused on an image sensor plane using a region apart from the laser irradiating portion as an observation viewing field of the image sensor for reflected light. In FIG. 2, numeral 1 denotes a semiconductor laser, 2 denotes an optical system, 9 denotes a laser spot, 10 denotes a linear observation region, 11 denotes an imaging lens and 12 denotes a line sensor. In FIG. 2, the laser spot is a horizontally-long ellipse, but it may be linear. Also, the observation region is not necessarily linear and the sensor may be a two-dimensional image sensor. Preferable embodiment is a manner in which the laser beam forms a linear spot, the image sensor is a line sensor and the observation region is collimated with the linear spot.

In case laser irradiating spot 9 is arranged apart from the observation region of the image sensor as shown in FIG. 2, for example, incident light from the laser spot 13 reaches a subcutaneous tissue deeply and then returns to observation portion 14. In such a case, since data depending on the bloodstream of internal tissue can be obtained, it is possible to observe clearly a bloodstream variation synchronized with heart pulse even with a cold fingertip.

Figure 4:
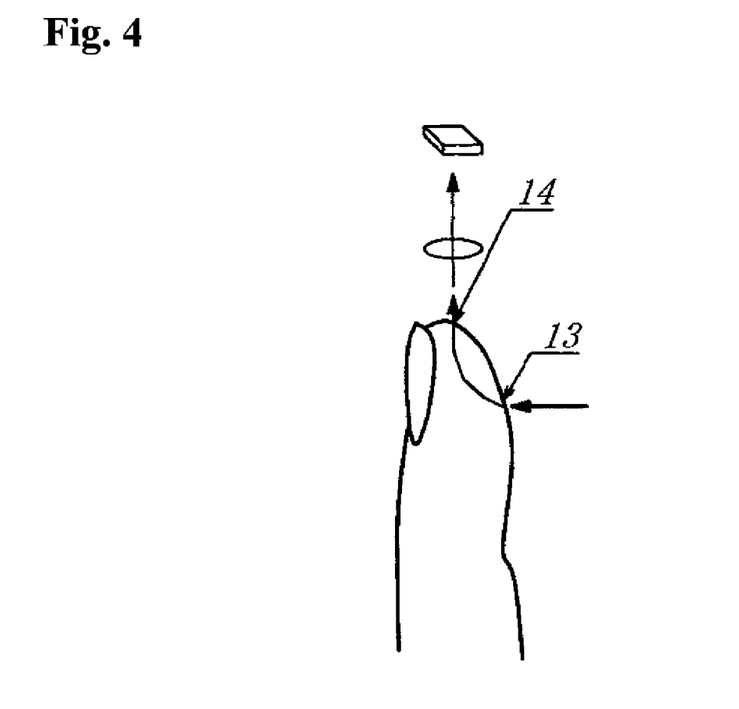
(FIG. 4) A diagram showing another example of a relationship of a laser irradiating spot and an observation position of an image sensor according to the present invention.
Figure 5:
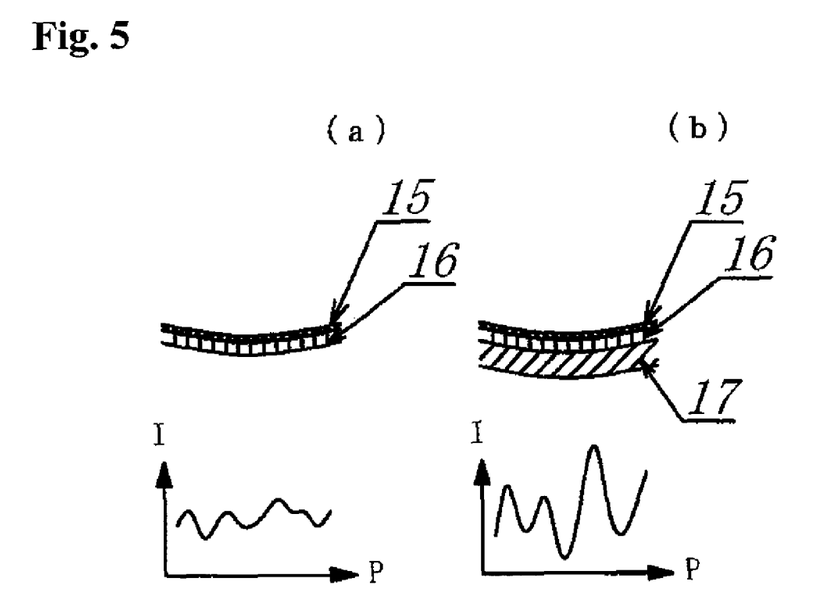
(FIG. 5) A diagram showing a signal of a liner sensor obtained from a subcutaneous blood vessel layer and a stratum corneum of finger.

Or, when a laser is irradiated to a center portion of a finger pad and a sensor is arranged in the side of a fingertip, for example, as shown in FIG. 4, a waveform of the bloodstream becomes more stable since incident light from laser spot 13 is received at observation position 14 after propagating a long distance inside of tissue. In FIG. 4, a laser may be irradiated to a fingertip portion of the finger pad, and an observation region of an image sensor may be arranged in a center portion of the finger pad Further, another preferable embodiment of the present invention includes an added function of detecting a counterfeited finger by detecting a signal waveform representing an intensity distribution of an amount of light received at each pixel of at least one row on the image sensor and comparing the signal waveform with a pre-set signal waveform of a living finger. The embodiment will be described with reference to FIG. 5. In FIG. 5, numeral 15 denotes a blood vessel layer under skin, 16 denotes a horny layer and 17 denotes a thin film made of silicone or the like.

FIG. 5(a) is a graph showing the signal of a line sensor obtained from subcutaneous blood vessel layer 15 and horny layer 16 of a normal finger wherein the horizontal axis P represents a pixel position and the vertical axis I represents light signal intensity. FIG. 5(b) is a graph showing a signal obtained from a finger with a thin film made of silicone or the like affixed thereto. As is clear from the graph, the waveform shows high-contrast. In general, when a laser is irradiated to a layer without a bloodstream, i.e., a layer in which particles scattered do not move internally, static speckles are formed upon occurring interference of reflected and scattering light on an image plane. Therefore, when a light intensity distribution is scanned by a line sensor etc., a signal waveform with high-contrast as shown in the graph of FIG. 5(b) is obtained and the waveform does not change since the pattern is static.

However, when many blood cells move internally, conditions of interference at each point of the image plane vary constantly, that is, interference occurs at one time in a coordinate phase and, at another time, in an antiphase. Therefore, a light-dark pattern varies with time. Actually, since the pattern varies rapidly reaching several kilohertz, light signals are integrated within the exposure time of the image sensor and accordingly the obtained image blurs. Consequently, the contrast decreases as shown in the graph of FIG. 5(a). When a tissue without a bloodstream is affixed to the surface of a finger, an image resembling a static image of speckles is obtained since scattering particles without movement exist in front of the finger, and the thus-obtained scattering signal has high-contrast as shown in the graph of FIG. 5(b). By utilizing the results, it is possible to identify an artificial material out of a pre-determined reference value such as a reference available to a living body.

The embodiment shown in FIG. 5, that is, a function that detects a counterfeited finger by detecting a signal waveform representing an intensity distribution of an amount of light received at each pixel of at least one row in the image sensor plane and comparing the signal waveform with a pre-set signal waveform of a living finger, can be incorporated to the inventions described in embodiments 1-4 of the present invention. However, the embodiment can also be incorporated directly to a conventional personal authentication method utilizing in subcutaneous bloodstream measurement.

That is, the conventional personal authentication method may include a function that detects a counterfeited finger by detecting a signal waveform representing an intensity distribution of an amount of light received at each pixel of at least one row in the image sensor plane at the appropriate time, that is, before, after or during each operation for authentication and comparing the signal waveform with a pre-set signal waveform of a living finger. Thereby, counterfeited fingers can be distinguished clearly from the standard finger of an individual.

Figure 6:
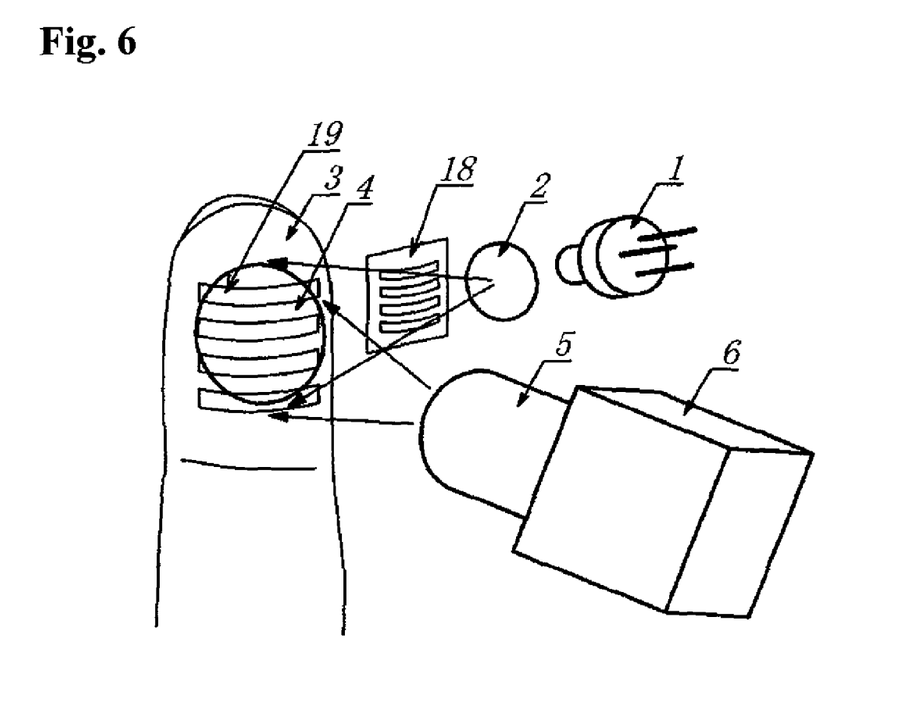
(FIG. 6) A diagram showing another embodiment in which a lattice-like laser spot is formed on a finger pad.

Although the present invention is described with reference to an example using a line sensor in the above explanation, in another embodiment of the present invention, a two-dimensional image sensor such as a TV camera can also be used according to a conventional method. In particular, lattice-shaped laser spot 19 may be formed by irradiating a laser onto a finger pad through masking shield 18 with a number of horizontally-long slits as shown in FIG. 6. In this case, if the horizontally-long spot is arranged in the same direction as a scanning line of the sensor, and data on the spot is analyzed, it is possible to detect the bloodstream and the time variation thereof on the surface layer of the finger pad. Alternatively, if data between each spot is analyzed, it is possible to detect the bloodstream and the time variation thereof on the internal layer of the finger pad. Personal authentication with very high accuracy can be carried out by comparison-checking the data with pre-registered personal data or by comparing/determining the data with a pre-determined reference. In such a case, masking shield 18 may be inserted only upon taking an internal bloodstream distribution, but it is not inserted upon taking a fingerprint image on the basis of the blood stream. The insertion of masking shield 18 can be switched with time.

In the present invention, a conventional technique comprising; expanding a laser beam and irradiating the expanded laser beam to a finger pad, focusing light reflected from a subcutaneous blood vessel layer on an image sensor plane as laser speckles using an optical system, calculating an amount representing a rate of time variation of light intensity received at each pixel of the laser speckles, setting a numerical value thus obtained as a two-dimensional map to thereby obtain a bloodstream map of the finger pad, and comparison-checking the bloodstream map with pre-registered data of an individual, includes a method of irradiating a laser beam with a specified wave length to a finger pad and a method of irradiating a plurality of laser beams differing in wave length to a finger pad simultaneously or sequentially so as to obtain a superimposed bloodstream speed map or a plurality of bloodstream speed maps with reference to light reflected from subcutaneous and internal tissue blood vessel layers.

The distance that a laser reaches into tissue varies with the wavelength. A laser with a short wavelength such as visible light gives only a distribution of the bloodstream near a finger surface, that is, a fingerprint pattern. While, a laser with a long wavelength such as near-infrared light gives a bloodstream map reflecting an internal bloodstream distribution since it reaches internal tissue deeply. The internal bloodstream distribution varies from person to person and is difficult to be counterfeited. When this is added to authentication data, the accuracy of personal verification is improved due to a synergistic effect. The present invention described above can be applied to such a conventional technique. For example, when two types of bloodstream maps are required by using a near-infrared laser beam capable of reaching internal tissue of a finger pad and a visible laser beam being easily absorbed by the subcutaneous stratum corneum, and measuring the bloodstream maps of the finger pad obtained from the respective reflected lights at the same time or in sequence, each irradiating spot may be arranged separate from each observation region regarding the respective lasers.

In accordance with the present invention, there is provided a device for carrying out the personal authentication method described above. The device of the present invention is a personal authentication device through the measurement of the subcutaneous bloodstream comprising: one or two irradiating means for expanding a laser beam and irradiating the expanded laser beam to a finger pad; light receiving means that has many pixels and receives light reflected from a subcutaneous blood vessel layer of the finger pad; storage means for storing the output of each pixel achieved by the light receiving means; calculation means for calculating an amount representing a rate of time variation of light intensity received at each pixel from the storage content of the storage means; second storage means for storing a two-dimensional distribution of the calculation result achieved at each pixel as a bloodstream map; and means for comparing the bloodstream map stored in the second storage means with the pre-registered personal data of an individual, wherein said irradiating means and light receiving means are arranged so that a region for irradiating the expanded laser beam is located separate from an observation region of the image sensor for light reflected.

Also, another device of the present invention is a personal authentication device through the measurement of the subcutaneous bloodstream comprising: one or two irradiating means for expanding a laser beam and irradiating the expanded laser beam to a finger pad; light receiving means that has many pixels and receives light reflected from a subcutaneous blood vessel layer of the finger pad; storage means for storing the output of each pixel achieved by the light receiving means; calculation means for calculating an amount representing a rate of time variation of light intensity received at each pixel from the storage content of the storage means; second storage means for storing a two-dimensional distribution of the calculation result achieved at each pixel as a bloodstream map; means for comparing the bloodstream map stored in the second storage means with the pre-registered personal data of an individual; means for calculating the time variation of an average bloodstream in the whole area or some area and comparing the time variation concerned with a predetermined reference for identification, wherein said irradiating means and light receiving means are arranged so that a region for irradiating the expanded laser beam is located apart from an observation region of the image sensor for reflected light.

The above-described personal authentication device may contain a means for detecting a counterfeited finger by detecting a signal waveform representing an intensity distribution of an amount of light received at each pixel of at least one row in the image sensor plane and comparing the signal waveform with a pre-set signal waveform of a living finger.

Further, another embodiment of the present invention is a personal authentication device through the measurement of the subcutaneous bloodstream comprising: one or two irradiating means for expanding a laser beam and irradiating the expanded laser beam to a finger pad; light receiving means that has many pixels and receives light reflected from a subcutaneous blood vessel layer of the finger pad; storage means for storing the output of each pixel achieved by the light receiving means; calculation means for calculating an amount representing the rate of time variation of the light intensity received at each pixel from the storage content of the storage means; second storage means for storing a two-dimensional distribution of the calculation result achieved at each pixel as a bloodstream map; and means for comparing the bloodstream map stored in the second storage means with pre-registered personal data individuals, wherein the device further includes means for detecting a counterfeited finger by detecting a signal wave representing an intensity distribution of an amount of light received for each pixel of at least one row in the image sensor plane and comparing the signal waveform with a pre-set signal waveform of a living finger.

For example, as the irradiation means, light emitted from a semiconductor laser is expanded through a lens and irradiated to a broad area of a finger pad at a stroke. As the light receiving means, an image sensor such as a line sensor, an area sensor or the like is used. An electrical signal from the sensor is subjected to A/D conversion, and then stored in a storage portion of a microcomputer or personal computer. An image signal is continuously taken into the storage portion over several seconds, and the difference between two sequential images is determined according to a program set in the microcomputer or the personal computer in advance to calculate the speed of the time variation of the amount of received light. Alternatively, the speed of the time variation of the received light amount is calculated by using the property that when the blurring rate of the image is increased, that is, the light amount varies at high speed within an exposure time of the image sensor, the signal is integrated and thus the difference in two display frames is conversely reduced. The calculation result may be displayed as a two-dimensional color map on the screen of the personal computer according to the arrangement of the respective pixels. As the means of comparing the calculation value or the fingerprint pattern displayed on the display means with pre-registered personal fingerprint patterns for identification, various kinds of well-known means may be used. Furthermore, the time variation of the average bloodstream value in some area of the finger pad over several seconds is determined, and for example, the waveform, amplitude, period or the like of the variation of the bloodstream may be used as a reference for comparison and identification.

INDUSTRIAL APPLICABILITY

According to the personal authentication method of the present invention, counterfeiting is difficult because a complicated fingerprint pattern and living body information are combined with each other. By making use of this advantage, the personal authentication method of the present invention can be applied to an entrance-and-exit check of facilities to which high-level security control is required, immigration control, etc.

The invention claimed is:
1. A personal authentication method through measurement of a subcutaneous bloodstream comprising:
   expanding a laser beam and irradiating the expanded laser beam to a finger pad;
   focusing light reflected from a subcutaneous blood vessel layer onto an image sensor plane as laser speckles by using an optical system;
   determining an amount representing a rate of time variation of light intensity received at each pixel point in the laser speckles and setting a numerical value thus obtained as a two-dimensional map to thereby achieve obtain a bloodstream map of the finger pad;
   comparison-checking a fingerprint pattern appearing as the bloodstream map with pre-registered personal data for authentication; and calculating time variation of an average bloodstream in the whole area or some area, and comparing the time variation concerned with a predetermined reference for authentication, wherein said laser speckles are focused onto the image sensor plane using a region separate from a region irradiated by the laser beam as an observation region of the image sensor, the laser beam forms a linear spot, the image sensor is a linear sensor and the linear spot is arranged in parallel with the observation region of the linear sensor.

2. The personal authentication method through the measurement of the subcutaneous bloodstream according to claim 1, wherein the laser beam is made to irradiate a center portion of the finger pad and the observation region of the image sensor is arranged in a fingertip side of the finger pad.

3. The personal authentication method through the measurement of the subcutaneous bloodstream according to claim 1, wherein the laser beam is made to irradiate a fingertip portion of the finger pad and the observation region of the image sensor is arranged in a center portion of the finger pad.

4. The personal authentication method through the measurement of the subcutaneous bloodstream according to claim 1, wherein the method further includes a function of detecting a counterfeited finger by detecting a signal waveform representing an intensity distribution of an amount of light received at each pixel of at least one row in the image sensor plane and comparing the signal waveform with a pre-set signal waveform of a living finger.

5. A personal authentication device through measurement of a subcutaneous bloodstream comprising:
one or two irradiating means for expanding a laser beam and irradiating the expanded laser beam to a finger pad;
light receiving means that has many pixels and receives light reflected from a subcutaneous blood vessel layer of the finger pad;
storage means for storing the output of each pixel achieved by the light receiving means;
calculation means for calculating an amount representing a rate of time variation of light intensity received at each pixel from storage content of the storage means;
second storage means for storing a two-dimensional distribution of a calculation result achieved at each pixel as a bloodstream map;
means for comparing the bloodstream map stored in the second storage means with pre-registered personal data for authentication;
means for calculating time variation of an average bloodstream in the whole area or some area and comparing the time variation concerned with a predetermined reference for authentication,
wherein a region for irradiating the expanded laser beam in said irradiating means is arranged separate from an observation region of an image sensor for reflected light in said light receiving means,
the irradiating means irradiates the laser beam as a linear spot,
the light receiving means is a line sensor and
the linear spot is arranged in parallel with an observation region of the linear sensor.

6. The personal authentication device through the measurement of the subcutaneous bloodstream according to claim 5, wherein the device further includes means for detecting a counterfeited finger by detecting a signal waveform representing an intensity distribution of an amount of light received at each pixel of at least one row in the image sensor plane and comparing the signal waveform with a pre-set signal waveform of a living finger.

7. A personal authentication method through measurement of a subcutaneous bloodstream comprising:
expanding a laser beam and irradiating the expanded laser beam to a finger pad;
focusing light reflected from a subcutaneous blood vessel layer onto an image sensor plane as laser speckles by using an optical system;
determining an amount representing a rate of time variation of light intensity received at each pixel point in the laser speckles and setting a numerical value thus achieved obtained as a two-dimensional map to thereby obtain a bloodstream map of the finger pad; and
comparison-checking a fingerprint pattern appearing as the bloodstream map with pre-registered personal data for authentication,
wherein the laser beam is irradiated to the finger pad through a masking shield with a number of horizontally-long slits to form a lattice-shaped laser spot,
the spot is arranged in the same direction as a scanning line of the sensor, and
data on the spot is analyzed to detect a surface layer bloodstream of the finger pad and time variation thereof or
data between each spot is analyzed to detect an internal layer bloodstream of the finger pad and time variation thereof.

8. A personal authentication method through measurement of a subcutaneous bloodstream comprising:
expanding a laser beam and irradiating the expanded laser beam to a finger pad;
focusing light reflected from a subcutaneous blood vessel layer onto an image sensor plane as laser speckles by using an optical system;
determining an amount representing a rate of time variation of light intensity received at each pixel point in the laser speckles and setting a numerical value thus obtained as a two- dimensional map to thereby obtain a bloodstream map of the finger pad;
comparison-checking a fingerprint pattern appearing as the bloodstream map with pre- registered personal data for authentication; and
calculating a time variation of an average bloodstream in the whole area or some area, and comparing the time variation concerned with a predetermined reference for authentication,
wherein the laser beam is irradiated to the finger pad through a masking shield with a number of horizontally-long slits to form a lattice-shaped laser spot,
the spot is arranged in the same direction as a scanning line of the sensor, and
data on the spot is analyzed to detect a surface layer bloodstream of the finger pad and time variation thereof or
data between each spot is analyzed to detect the bloodstream and time variation thereof.

9. The personal authentication method through the measurement of the subcutaneous bloodstream according to claim 2, wherein the method further includes a function of detecting a counterfeited finger by detecting a signal waveform representing an intensity distribution of an amount of light received at each pixel of at least one row in the image sensor plane and comparing the signal waveform with a pre-set signal waveform of a living finger.

10. The personal authentication method through the measurement of the subcutaneous bloodstream according to claim 3, wherein the method further includes a function of detecting a counterfeited finger by detecting a signal waveform representing an intensity distribution of an amount of light received at each pixel of at least one row in the image sensor plane and comparing the signal waveform with a preset signal waveform of a living finger.

* * * * *